(12) United States Patent
Ardrey, Jr.

(10) Patent No.: US 8,640,712 B2
(45) Date of Patent: Feb. 4, 2014

(54) BOLUS

(76) Inventor: William E. Ardrey, Jr., Cleveland, OK (US)

( * ) Notice: Subject to any disclaimer, the term of this patent is extended or adjusted under 35 U.S.C. 154(b) by 460 days.

(21) Appl. No.: 12/788,128

(22) Filed: May 26, 2010

(65) Prior Publication Data

US 2010/0300462 A1 Dec. 2, 2010

Related U.S. Application Data

(60) Provisional application No. 61/181,394, filed on May 27, 2009.

(51) Int. Cl.
*A61B 19/00* (2006.01)
*A61B 5/07* (2006.01)

(52) U.S. Cl.
USPC .......................................... 128/899; 600/302

(58) Field of Classification Search
USPC .................................. 128/899; 600/302, 549
See application file for complete search history.

(56) References Cited

U.S. PATENT DOCUMENTS

| | | | |
|---|---|---|---|
| 3,893,111 A | 7/1975 | Cotter | |
| 4,695,435 A * | 9/1987 | Spector | 422/124 |
| 4,854,328 A | 8/1989 | Pollack | |
| 5,872,516 A | 2/1999 | Bonge, Jr. | |
| 5,984,875 A | 11/1999 | Brune | |
| 6,012,415 A | 1/2000 | Linseth | |
| 6,099,482 A | 8/2000 | Brune et al. | |
| 6,371,927 B1 * | 4/2002 | Brune et al. | 600/549 |
| 2006/0030754 A1 * | 2/2006 | Iddan | 600/153 |
| 2006/0177291 A1 * | 8/2006 | Kienzl et al. | 414/331.15 |
| 2008/0316020 A1 * | 12/2008 | Robertson et al. | 340/539.12 |
| 2009/0048498 A1 * | 2/2009 | Riskey | 600/302 |

* cited by examiner

*Primary Examiner* — Christine Matthews
*Assistant Examiner* — Kaylee Wilson
(74) *Attorney, Agent, or Firm* — McAfee & Taft

(57) ABSTRACT

A bolus for monitoring the parameters of an animal. The bolus will sense selective parameters and will send signals representative of those parameters to a receiver. The bolus includes sensors for sensing a number of parameters such as temperature, pH and movement. The power of the signal inside the animal is greater than that outside the animal since the signal is attenuated by the structure of the animal.

15 Claims, 2 Drawing Sheets

BOLUS

CROSS REFERENCE TO RELATED APPLICATION

This application incorporates by reference and claims the benefit of U.S. Provisional Application 61/181,394 filed on May 27, 2009.

BACKGROUND

This disclosure relates to a system and apparatus for monitoring physiological and other parameters of animals. Specifically, this disclosure relates to a bolus which will sense and transmit information from inside an animal.

There are currently a number of prior art devices designed to remotely monitor the core temperature of animals. One such device is commonly referred to as a bolus, which is ingestible by animals. Boluses are designed to sense very slight temperature changes, which often will signal a change in the physiological state of an animal. Detection of such changes can allow early action to quickly detect and treat illnesses, take quick action to prevent the spread of diseases and sicknesses, and to monitor breeding conditions.

U.S. Pat. No. 6,371,927 to Brune et al., discloses a bolus for monitoring physiological conditions such as temperature. The bolus described in Brune et al. will transmit physiological conditions along with a unique identification code associated with the bolus and thus associated with the animal to a receiving unit. The receiving unit will receive transmitted signals and provide a readout of the transmitted data. The receiver may be located in a centralized location or, according to Brune et al., may be a hand-held receiving unit. The Brune et al. bolus is described as field programmable, but also may be programmed while in the rumen of a ruminating animal. The bolus is designed for periodic data transmission and may also be queried from the receiver location. The bolus goes into a sleep mode for power conservation when data is not being transmitted. While there are prior art devices such as that described by Brune to remotely monitor the core temperature of animals, there is a continuing need for devices that will monitor and provide physiological information for animals quickly, efficiently and accurately.

BRIEF DESCRIPTION OF THE DRAWINGS

FIG. 3 is a schematic showing transceivers with which the bolus may communicate.

DESCRIPTION OF A PREFERRED EMBODIMENT

Figure 1:
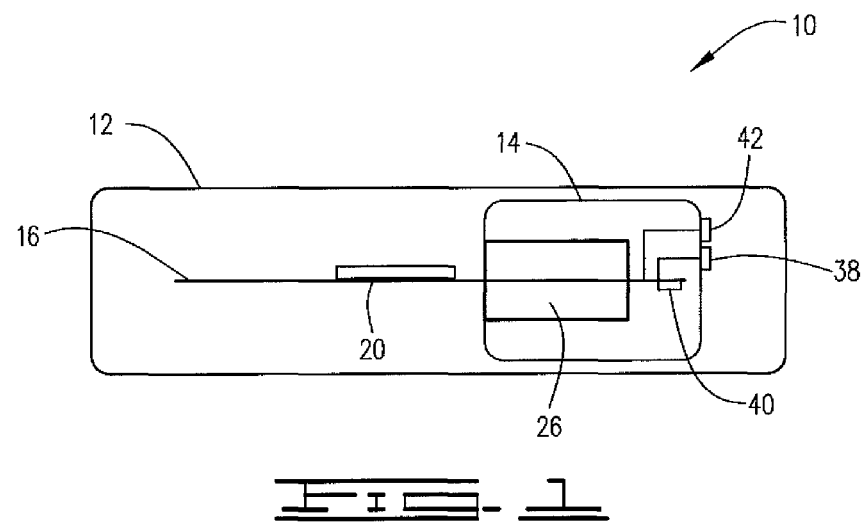
FIG. 1 schematically shows a bolus. The outer shell is cut away to provide a view of the interior of the bolus.

As shown in FIG. 1, ingestible bolus 10 is a generally pill-shaped bolus that may be ingested by an animal. Bolus 10 has a housing 12, which is preferably plastic, for example, ABS or Nylon. A ballast 14 which may comprise a ferrous material is disposed in housing 12. Ballast 14 may be magnetized. Ingestible bolus 10 will include circuit boards, an antenna and a battery along with sensors which may be for example temperature sensors, pressure sensors, sensors that will detect certain chemicals, accelerometers, pH sensors and other sensors that may be utilized to measure physiological or other characteristics. In the embodiment shown, a printed circuit board 16 provides structure to hold circuits, a power source, microprocessor, antenna, amplifiers, transmitters and other components.

Figure 2:
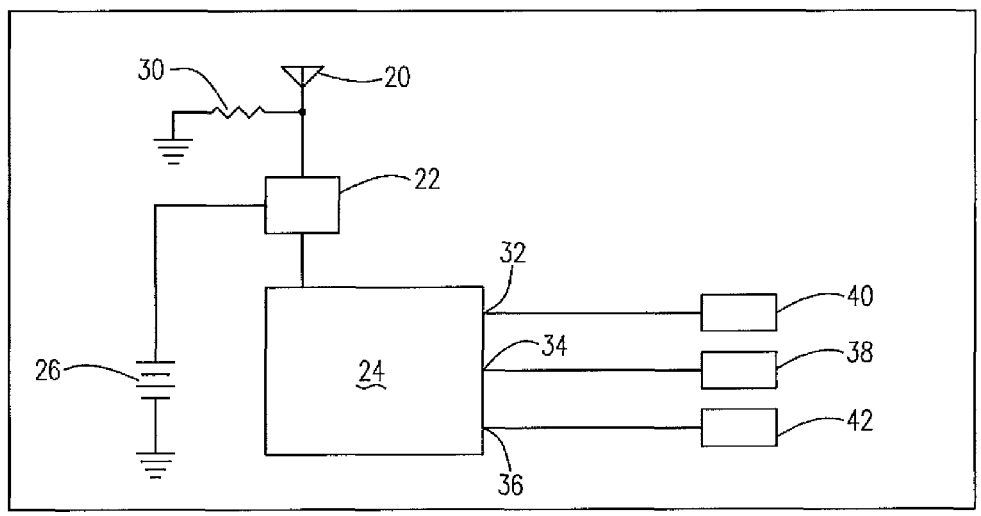
FIG. 2 schematically shows internal components of the bolus.
Figure 2:
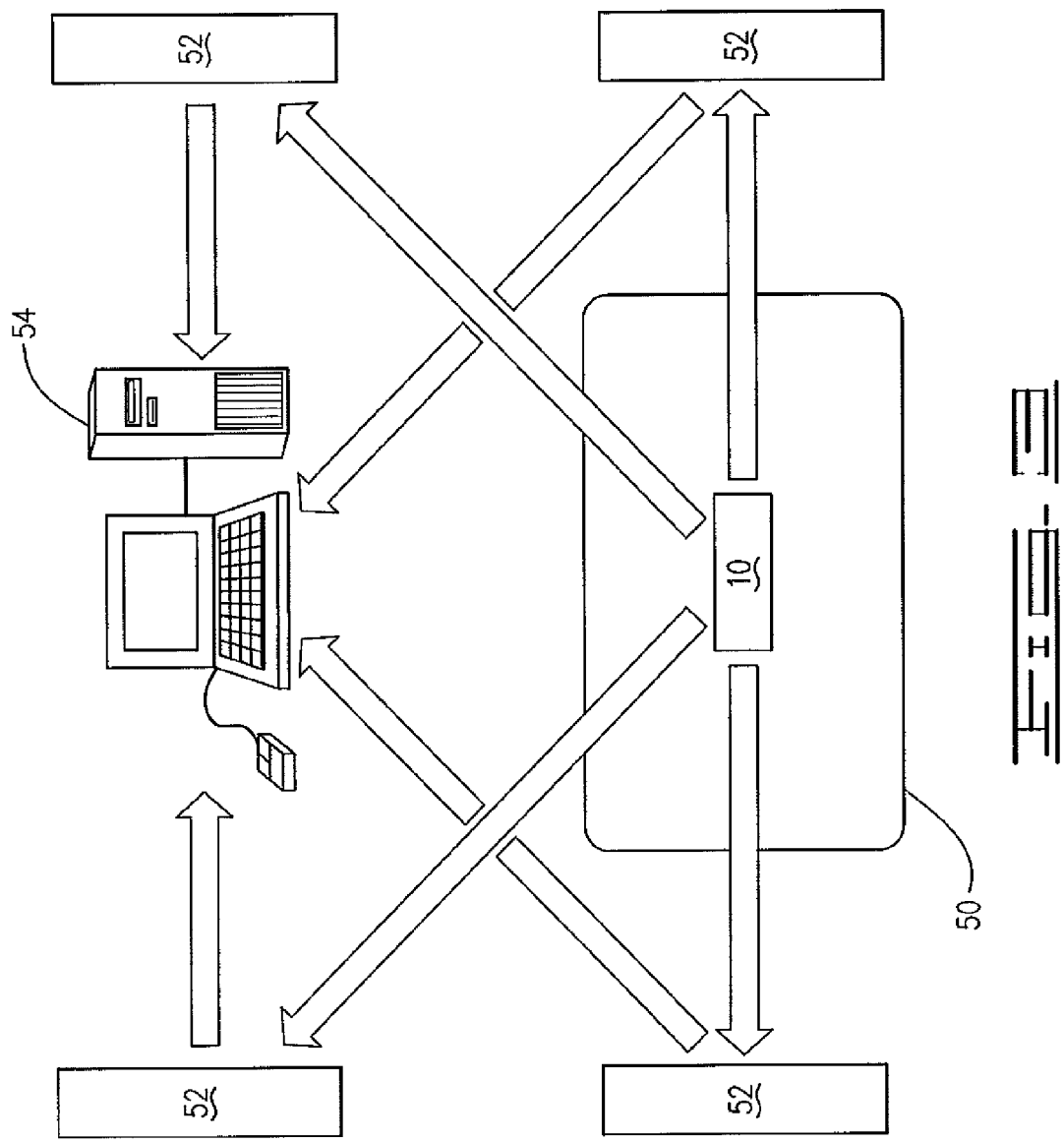

FIG. 2 is exemplary of a system that may be utilized with the current invention. Bolus 10 may include an antenna 20, an RF transmitter 22, a microprocessor 24 with internal memory and embedded software and a battery 26 for power. Bolus 10 will have a unique identification associated therewith which may be stored in microprocessor 24. RF transmitter 22 also acts as an RF amplifier, and may be referred to as such, or simply as RF circuit 22. RF transmitter 22 is tuned to the desired UHF frequency in a typical manner by way of a resistor/capacitor circuit, for example, resistor 30, or resistor/inductor circuit or other acceptable means. Antenna 20 is connected to the RF transmitter 22 and is tuned and matched to the circuit by means known in the art. For example, the length of antenna 20 can be adjusted to match the desired frequency or the antenna circuit can be matched to the required impedance of the RF transmitter through the tuned resistor/capacitor or resistor/inductor circuit 30.

Microprocessor 24 may have a plurality of digital and/or analog ports, which may also be referred to as input channels associated therewith. Microprocessor 24 may have, for example, ports 32, 34 and 36, which may be digital or analog ports, or may be digital/analog ports. Port 34 may be a digital port 34. An ultraviolet (UV) light sensor 38 may be connected to communicate through digital port 34. UV light sensor 38 is capable of producing different voltage levels depending on the presence or absence of UV light.

Bolus 10 will also include at least one sensor for measuring a selected physiological parameter. Sensor 40 may be, for example, a temperature sensor 40 that measures temperature. The sensed temperature is communicated through input port 32, which may be an analog port in a manner known in the art. Generally, the temperature sensor will produce voltage changes when a temperature change is experienced, and the voltage change is communicated through port 32.

A user can excite UV sensor 38 by way of a UV light source and can communicate data therethrough to the microprocessor. The communicated data can be transmitted to microprocessor port 34 via the UV light in such a pattern that the embedded software can make modifications to the performance of the microprocessor or change the unique identification. For example, the temperature sampling rate can be increased, dates of birth or other data of interest can be added to the internal memory of the bolus. The embedded software in microprocessor 24 can also monitor UV port 34 from time to time and if the UV port remains without a significant voltage level that indicates the non-presence of UV light, the bolus 10 can start transmitting at a maximum power, since the absence of UV light reflects that the bolus 10 has been ingested into an animal. As will be explained further, operation at a maximum power level may be necessary to overcome the natural attenuation of a signal due to the structure of the animal.

In addition to sensors for monitoring physiological parameters, other sensors can be utilized as well. Bolus 10 may thus include an analog port 36 to which a sensor may be connected. The sensor may be of a type that produces a change in a voltage level to indicate a particular parameter. For example, an accelerometer, or motion sensor 42 capable of producing change in voltage levels depending on the presence or absence of movement may be connected to analog port 36. Accelerometer 42 will produce higher voltage levels proportional to the amount of movement of the animal. The embedded software in microprocessor 24 will monitor analog port 36 from time to time, and if the voltage produced by accelerometer 42 is sufficient to indicate movement of the animal, the embedded software will record the event, and encode the information into the data system that will be sent via the RF transmitter 22 of bolus 10. The sensors 38, 40 and 42 may be inside housing 12, or may be positioned outside housing 12.

The current disclosure is also directed to a system for transmitting and receiving signals from bolus 10. Signals transmitted by bolus 10 are preferably sent at an ultra-high frequency, and may be signals that reflect the physiological or other parameters measured by bolus 10, such as temperature or movement as sensed by accelerometer 42. It is understood that pH and other parameters may be measured, and signals representing those parameters may be transmitted by the bolus. The system may include spread spectrum transceivers, peer to peer receivers that are capable of receiving and transmitting signals, and a base station which may consist of a receiver and associated processor for receiving, analyzing and displaying the signals in a digital or other readable format. Such an arrangement provides a reliable way to insure that all data is being received and reviewed and also provides for a quick and efficient transmission and receipt of the data.

Signals sent by bolus 10 are preferably transmitted on an ultra-high frequency, for example, 300 MHz to 3 GHz. Bolus 10 disclosed herein is capable of transmitting at such a frequency due to the use of tuned circuits, which, as described herein, includes matching the antenna to the specific environment. Utilizing an ultra-high frequency carrier decreases the transmission time required to transmit data streams that may consist of a large amount of data, for example, up to 256 bytes per bolus per transmission. With a frequency of 315 MHz and a baud rate of 4800, it would take approximately 100 milliseconds to transmit an entire data stream of 60 bytes. Because of the ultra-high frequency being utilized, the data will be sent quickly and there is less potential for collision or interference among signals. Prior art devices generally utilize a much lower frequency such as for example 27 MHz. Thus, with prior art devices data is transmitted at a much slower rate, which increases the possibility of interference, and collision with other signals. One reason prior devices utilize low frequencies is that a signal transmitted through the animal at a lower frequency is not as affected by the animal structure as a signal sent at ultra-high frequency.

It is understood that any signal sent by bolus 10 will be attenuated by muscle, tissue, bone, body fluids and other animal structure. It has been determined that such a structure of a ruminant animal will attenuate a signal approximately seventeen decibels (dB). Bolus 10 is designed to compensate for the attenuation of the signal by operating at a higher transmission dB after placement in an animal. Once ingested, bolus 10 operates at a dB power level such that the signal, after it passes through the animal is transmitted at approximately fourteen dB. To transmit the signal at the desired power, the bolus must transmit inside the animal at a much higher power, for example, 31 dB. A bolus operating at that power level when it is physically outside the animal may therefore potentially violate limits set by the Federal Communications Commission (FCC).

To accomplish the increased power necessary to achieve the 14 dB power but to prevent the bolus 10 from operating in excess of acceptable limits when it is outside the animal, bolus 10 is equipped with light sensor 38 connected to input port 34 of microprocessor 24 in the bolus. Microprocessor 24 may be, for example, an 8 or 16 bit processor that has both digital and analog input channels. The embedded software code in the microprocessor can analyze the input from the various sensor devices connected to the external ports or channels. Bolus 10 is programmed so that when sensor 38 is in the presence of a light source, UV light for example, bolus 10 will be in a first state. The first state may be a state in which bolus 10 has an RF power transmission rate that is less than the RF power transmission rate of the bolus 10 when inside the animal. The first state may be a dormant, non-operating state in which the RF power transmission rate is zero. When the bolus is ingested and thereby removed from the presence of UV light, the microprocessor will switch bolus 10 from the first state to a second state. In the second state, bolus 10 will have an RF power transmission rate that is higher than that in the first state. Bolus 10 is therefore fully operational and operates in the second state at a higher power level than when in the first state. When the voltage level at the port 34 is such that it indicates an absence of UV light for a predetermined period of time, bolus 10 will operate at an RF power transmission rate high enough to compensate for the attenuation by the animal structure. When bolus 10 is removed from the animal and is again exposed to UV light, it will cease operating, or may operate in the first state as described. If bolus 10 is to be reused, it can be reprogrammed to move to the second fully operational state when removed from UV light. Bolus 10 is therefore designed such that it will only operate in its second state in the absence of UV light and when the bolus is physically outside the animal, it will always be in the first state which may be a reduced RF power transmission state, or a dormant, non-operating state. While the absence of UV light is described herein as the trigger for causing bolus 10 to switch to an operating state, or to increase the power at which bolus 10 is operating, other methods may be used. For example, a sensed temperature change might be used as the event that activates the bolus 10, or increases the power at which bolus 10 operates.

As explained above, light sensor 38 may also be used to uniquely program bolus 10. Bolus 10 prior to ingestion by an animal will initially have a unique identification that represents a specific animal. Light sensor 38 may be used, if desired, to add unique programming to bolus 10. For example, an external light source in the UV wave length may be used to add unique information such as the age, weight, breed, date of birth, lineage or other desired unique information associated with the animal.

The measured and signaled parameters are useful for a variety of purposes. For example, an extended increase in temperature, for example, eight to ten hours, can indicate disease or sickness. An extended increase in the temperature in a number of cattle can indicate sickness or disease epidemic. Temperature increase is also a manner of estrous detection in that a slight increase in temperature may indicate that an animal, for example, a cow, is in heat. A drop in temperature may indicate that calving is about to begin. Bolus 10 may operate in a standard mode to measure and send signals at specified intervals representing measured temperatures. While the standard mode of operation will be to transmit signals at defined intervals, the bolus is designed such that it will send a signal based upon a triggering event. For example, an increase in temperature of a certain predetermined amount may trigger the bolus to send an immediate signal, and to begin sending information at more rapid intervals. In other words, the embedded software will schedule normal monitoring intervals. A predetermined normal temperature range will be a part of the information stored in the microprocessor memory. The recorded temperature will be compared against the stored normal temperature range. If the measured and recorded temperature is outside the normal range, the sampling rate, and transmission rate can be modified. If the temperature normalizes the bolus will after a defined time revert to its normal interval cycle. The same theory of operation can be utilized with other parameters. Other physiological parameters may be measured and transmitted as described. The accelerometer utilized with the bolus will indicate the amount of movement over a certain time. Increased movement along with increased temperature is likewise an indication that a cow is in heat. Thus, movement will be monitored and will be part of the information sent at defined intervals, and can also be a triggering event for an immediate transmission and more rapid than normal intervals.

The transmission range of bolus 10 may in some cases be limited by parameters like available power, ambient conditions and the physical distance of a receiver subsystem. For example, free range animals that have ingested bolus 10 may wander out of effective range of a receiver. If bolus 10 is not within range of a receiver system, transmitted data could go undetected. Temperature or other measured parameter or event is recorded based on the schedule of the embedded software within the microprocessor's available memory. A plurality of samples are recorded such that there is a history stored within bolus 10. The entire history of recorded events, the frequency at which the data was recorded, for example, once per hour, and the number of transmissions of the bolus, will be sent to the receiver and then relayed on to the base station and computer for analysis at periodic intervals. In other words, each time the bolus transmits data, a history of, for example, the previous twelve hours of activity and information may be transmitted. Thus, bolus 10 includes a memory such that the temperature or other measured parameters are stacked. When a signal is transmitted, it will include information concerning the immediate measurement, a number of previous measurements, the frequency in time of the samples and the number of previously sent samples. Such data will be sent at prescribed intervals so that if one signal is not received, a constant history of temperature or other information is received and maintained.

A schematic is set forth in FIG. 3. Bolus 10 is ingested into an animal 50, which may be a bovine animal, or other ruminant animal in which it is desired to use bolus 10. Bolus 10 will monitor and measure desired parameters as described herein. The microprocessor 24 will receive and process the information which may be for example a voltage change. Microprocessor 24 will convert the information to a value representative of the parameter, for example temperature or pH. Microprocessor 24 will pass the value through to the RF transmitter 22, which will send a signal representative of the value. The signal may be received by one or more of a plurality of transceivers 52. Transceivers 52 will send the signal to a base station 54. Base station 54 may provide a printout, and/or a display with a readable display. The signal sent by bolus 10, and ultimately received by base station 54 may include a reading not just of an immediate measurement, but of several stacked values generated at specified time intervals. Thus if an animal is out of range of all of transceivers 52 for a time period, the signal sent when the animal moves back into range will include a historical record of the desired parameter.

Thus, it is seen that the apparatus and methods of the present invention readily achieve the ends and advantages mentioned as well as those inherent therein. While certain preferred embodiments of the invention have been illustrated and described for purposes of the present disclosure, numerous changes in the arrangement and construction of parts and steps may be made by those skilled in the art, which changes are encompassed within the scope and spirit of the present invention as defined by the appended claims.

What is claimed is:

1. A method of monitoring a selected physiological parameter of an animal comprising:
   causing the animal to ingest a bolus, the bolus including a microprocessor;
   measuring the selected parameter with the bolus at specified time intervals;
   storing a plurality of the measurements such that there is a history of the selected physiological parameter stored within the bolus wherein said history is maintained for at least a predetermined period of time; and
   transmitting a signal at prescribed intervals such that there is a plurality of signals transmitted and a history associated with each prescribed interval, each said signal containing at least the history associated with the most recent prescribed interval and the history associated with prior prescribed intervals occurring within the predetermined period of time, wherein the predetermined period of time is greater than the prescribed intervals such that, if one such signal is not received, a constant history for the predetermined period of time is received and maintained.

2. The method of claim 1, further comprising:
   automatically switching the bolus from a dormant, non-operating state to an operating state upon ingestion by the animal.

3. The method of claim 1, wherein the animal has a movement pattern and further comprising:
   monitoring the movement pattern of the animal with the bolus; and
   sending a signal representative of the movement pattern.

4. The method of claim 1, wherein the signal transmitted by the bolus is transmitted at an ultra-high frequency.

5. The method of claim 4, wherein the signal is transmitted at a frequency of at least 300 MHz.

6. The method of claim 4 further comprising:
   automatically switching the bolus from a first state outside the animal to a second state when ingested by the animal, wherein in the first state the bolus operates at a first RF transmission power and in the second state the bolus operates at an increased RF transmission power.

7. The method of claim 1 further comprising:
   determining whether the measured parameter is outside a predetermined range; and
   decreasing the specified time intervals at which the selected parameter is measured if the measured parameter falls outside the predetermined range for the selected parameter.

8. The method of claim 7 wherein the determining is made by the bolus by reference to the predetermined range; and wherein said decreasing the specific time intervals is carried out by the bolus in response to its determination that the measured parameter is outside the predetermined range.

9. The method of claim 1 further comprising:
   receiving the signal and providing a readable display of the measured parameter.

10. The method of claim 1 wherein the history further includes the number of signals within the predetermined period of time.

11. The method of claim 1, further comprising:
    automatically switching the bolus from a dormant, non-operating state to an operating state upon ingestion by the animal wherein the switching is based on signals from a temperature sensor or from a light sensor.

12. The method of claim 11 wherein the automatically switching the bolus from a dormant, non-operating state to an operating state is based on a signal from said light sensor and said light sensor is a UV sensor which senses UV light.

13. The method of claim 12 wherein in the dormant non-operating state the bolus does not transmit the signal and in the operating state the signal is an ultra-high frequency signal.

14. The method of claim 13 wherein the bolus automatically reverts to a dormant, non-operating state when it is removed from the animal.

15. The method of claim 14 wherein said ultra-high frequency signal is at an RF transmission power sufficient to result in about a fourteen dB signal after it passes through the animal.

* * * * *